United States Patent [19]

Quinlan

[11] 4,057,390
[45] Nov. 8, 1977

[54] SULFUR-CONTAINING BIS-QUATERNARIES

[75] Inventor: Patrick M. Quinlan, Webster Groves, Mo.

[73] Assignee: Petrolite Corporation, St. Louis, Mo.

[21] Appl. No.: 689,134

[22] Filed: May 24, 1976

[51] Int. Cl.$^2$ .................. C23F 11/00; C09K 3/00; C23F 9/00
[52] U.S. Cl. .................. 21/2.7 R; 252/391; 252/392; 252/8.55 E; 252/180; 21/2.5 R
[58] Field of Search .......... 252/391, 402, 390, 388, 252/392, 8.55 C, 8.55 E, 148, 151; 21/2.5 R, 2.7 R

[56] References Cited

U.S. PATENT DOCUMENTS

| | | | |
|---|---|---|---|
| 3,197,403 | 7/1965 | Riggs, Jr. | 252/391 |
| 3,809,655 | 5/1974 | Williams | 252/8.55 E X |
| 3,920,392 | 11/1975 | Harada et al. | 252/8.55 E X |
| 3,982,894 | 9/1976 | Annand et al. | 252/390 |
| 3,992,306 | 11/1976 | Diery | 252/391 X |

Primary Examiner—Leland A. Sebastian
Assistant Examiner—Josephine Lloyd
Attorney, Agent, or Firm—Sidney B. Ring; Hyman F. Glass

[57] ABSTRACT

This invention relates to sulfur-containing Bis-Quaternaries of the idealized formula

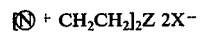

where Ⓝ is a quaternary amino group, Z is a sulfur-containing group, for example S, SO, SO$_2$ and X is an anion; to methods of preparing such compounds; and to uses of such compounds.

10 Claims, No Drawings

SULFUR-CONTAINING BIS-QUATERNARIES

I have discovered that sulfur-containing Bis-Quaternaries of the idealized formula

[ ⊕CH₂CH₂]₂Z · 2X⊖ where Ⓝ is a quaternary amino group, Z is a sulfur-containing group for example S, SO, SO₂ and X is an anion have a wide variety of uses, including their uses as corrosion inhibitors, microbiocides, etc.

In the present invention, the Bis-Quaternaries are prepared by reacting salts of tertiary amines (either linear or cyclic) with divinyl sulfur compounds.

The equation may be ideally presented as follows:

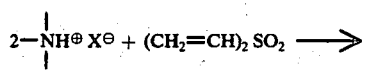

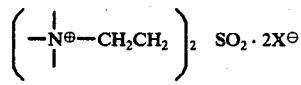

The tertiary nitrogen group represented by

may be part of a linear configuration or a cyclic configuration ⟨N.

Representative formulae are as follows:
1. Aliphatic type amines

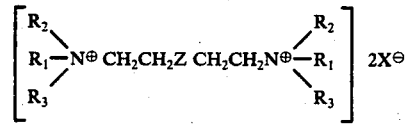

where R₁, R₂, R₃ are alkyl oxygen-containing alkyl groups such as alkyleneoxyalkylene, alkanol, etc., Z is

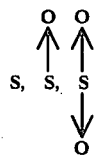

and X is an anion.
2. Cyclic amines:

where ⟨N is a cyclic tertiary amine moiety, Z is

and X is an anion.
Examples of the divinyl sulfur compounds are:

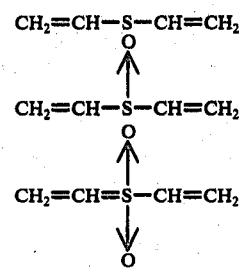

Any suitable tertiary amine can be employed, for example of the general formula

where R, R′, R″ which may be the same or different are groups that do not interfere with the reaction, for example, alkyl of 1-30 or more carbons, such as 1-18 or more carbons. In practice some of the alkyl groups may have low carbon content and others high carbon content of the fatty type such as in excess of 6 carbons. In addition 1 or more of the alkyl groups may be substituted, for example with hydroxyalkyl groups, etc.

Examples of aliphatic tertiary amines include the following: trimethyl amine, triethyl amine, tributyl amine, dioctyl methyl amine, didecyl methyl amine, dimethyl dodecyl amine, dimethyl hexadecyl amine, Armak DM12D, Armak DM14D, Armak DM18D, Armak DMCD, Armak DMTD, dihydroxyethyl dodecyl amine, triethanolamine and the like.

Any suitable cyclic tertiary amine can be employed, for example of the general formula

where all three of the nitrogen valences are substituted either by aromatic or non-aromatic valences. Thus the tertiary amine may be fully aromatic as in the case of pyridine, etc., or cyclic non-aromatic and aliphatic in the case of N-methyl morpholine, etc.

Examples of cyclic tertiary amines include the following:

Pyridine, 1-Picoline, 2-Picoline, 3-Picoline, 2-chloropyridine quinoline, isoquinoline, pyrimidine, benzidine, acridine, N-methylpiperidine, N-methyl morpholine, triethylenediamine, hexamethylenediamine, Union Carbide Alkyl Pyridine R, Reilly Tar Base HB, Koppers Co. QSR base and the like.

Any suitable acids that may be employed to form the tertiary amine salts including hydrohalic acids such as hydrochloric, hydrobromic, hydroiodic, etc.; sulfuric, phosphoric, nitric, hydrocarbon sulfuric acids such as methanesulfonic, organic acids such as formic, acetic, benzoic and the like.

In carrying out the reaction it is preferred to form the amine salt in situ, that is in a solvent such as ethanol or in a water-alcohol mixture in which it is soluble. To the solution of the amine salt is added the divinyl sulfur compound. The preferred temperature is about 20° to 50° C though higher or lower temperatures may be employed. A short period of reflux may be used to ensure complete reaction. In most cases the product is not isolated. The crude reaction mixtures are generally employed in the uses of this invention since in most instances the isolation and purification of the products is tedious and time consuming.

The invention may be illustrated by the following examples.

EXAMPLE 1

Divinyl sulfone 5.9g (0.05 mole) was slowly added to a solution of 10.8g (0.01 mole) of triethylamine hydrochloride in 25 ml. of ethanol. The reaction mixture becomes warm and crystals appeared upon standing. The crystals were filtered, washed with alcohol, and dried over $P_2O_5$. They were needlelike and hygroscopic.

Analysis: $(C_{16}H_{38}N_2SO_2Cl_2)$% Cl calc. = 18.1 % Cl Found = 18.2

The product had the structure:

[(C_2H_5)_3N^+CH_2CH_2SO_2CH_2CH_2N^+(C_2H_5)_3] 2 Cl^-

EXAMPLE 2

Divinyl sulfone 5.9g (0.05 mole) was slowly added to a solution of 24.9g (0.1 mole) of dimethyldodecylamine hydrochloride dissolved in 50 ml. of ethanol. After the addition was completed the reaction mixture was heated at reflux for 2 hrs. The solvent was taken off on a rotary evaporator leaving a waxy solid. The solid was filtered and washed with alcohol and dried in an oven at 70° C.

Analysis: $(C_{32}H_{70}N_2SO_2Cl_2)$ % Cl calc. = 11.5 % Cl found = 11.8

The product had the structure:

[C_{12}H_{25}N^+(CH_3)_2CH_2C_2SO_2CH_2CH_2(CH_3)_2N^+C_{12}H_{25}]2 Cl^-

EXAMPLE 3

19.7g of concentrated hydrochloric acid was slowly added with cooling to a solution of 47g (0.2 mole) of *Armak DMCD dissolved in a mixture of 34g of water and 20g of 2-propanol. To this solution was added 11.8g (0.1 mole) of divinyl sulfone. The resulting solution was heated at reflux for 4 hours. *Armak DMCD contains R, a mixture of $C_{10}$ through $C_{18}$ with a predominance of $C_{12}$ and $C_{14}$, $RN(CH_3)_2$.
*Armak DM14D contains R, a mixture of $C_{12}$, $C_{14}$ and $C_{16}$ with 90% being $C_{14}$, $RN(CH_3)_2$.

Example 4

19.7g of concentrated hydrochloric acid was slowly added with cooling to a solution of 49.0Og (0.2 mole) of *Armak DM14D dissolved in 35g of water and 21g of 2-propanol. To this solution was added 11.8g (0.1 mole) of divinyl sulfone. The resulting solution was heated at reflux for 4 hrs. In a similar manner the following examples were prepared.

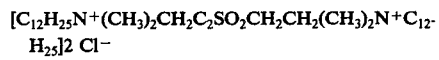

| Example | $R_1$ | $R_2$ | $R_3$ | $X^\ominus$ |
|---|---|---|---|---|
| 5 | $C_2H_4OH$ | $C_2H_4OH$ | $C_2H_4OH$ | Cl |
| 6 | $C_2H_5$ | $C_2H_5$ | $C_2H_5$ | Br |

-continued

| Example | $R_1$ | $R_2$ | $R_3$ | $X^\ominus$ |
|---|---|---|---|---|
| 7 | $C_{12}H_{25}$ | $C_2H_4OH$ | $C_2H_4OH$ | Cl |
| 8 | $CH_3$ | $CH_3$ | $CH_3$ | I |
| 9 | $C_8H_{17}$ | $C_8H_{17}$ | $CH_3$ | Cl |
| 10 | $C_{10}H_{21}$ | $C_{10}H_{21}$ | $CH_3$ | Cl |
| 11 | $C_{18}H_{37}$ | $CH_3$ | $CH_3$ | Cl |

EXAMPLE 12

Divinyl sulfone 5.9g (0.05 mole) was slowly added to a solution of 11.4g (0.1 mole) of pyridine hydrochloride in 25 ml. of ethanol. Upon standing overnight the solution crystallized. The crystals were filtered, washed with alcohol and dried over $P_2O_5$. They were white hydroscopic needles.

Analysis: $(C_{14}H_{18}N_2SO_2Cl_2)$ % Cl calc. = 20.3 % Cl found = 20.1

The product had the following structure:

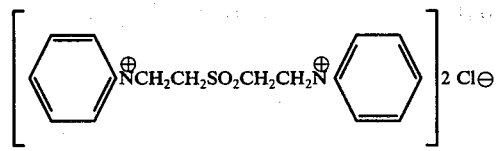

EXAMPLE 13

Divinyl sulfone 5.9g (0.05 mole) was slowly added to a solution of 16.5G (0.1 mole) of quinoline hydrochloride in 30 ml. of ethanol. The mixture crystallized upon standing. The orange crystals were filtered, washed with alcohol and dried over $P_2O_5$.

Analysis: $(C_{22}H_{22}N_2Cl_2SO_2)$ % Cl calc. = 15.8 % Cl found = 15.5

The product had the structure:

$C_9H_7$ = quinoline

EXAMPLE 14

To 50.4g (0.4 mole) of *Koppers QSR base dissolved in 50g of $H_2O$ and 17g of methanol was added, with cooling, 39.4g of concentrated hydrochloric acid. After the addition was completed, 23.6g (0.2 mole) of divinyl sulfone was slowly added. The mixture was heated to reflux and held there for 6 hours.
*Koppers QSR base is a crude mixture containing quinoline, isoquinoline, and 2-methyl quinoline.

EXAMPLE 15

To 34.0g (0.2 mole) of *Union Carbide Alkyl Pyridine R dissolved in 31g of water and 10g of 2-propanol was added, with cooling, 19.7g of conc, H Cl. Then 11.8g (0.1 mole) of divinyl sulfone was added. The reaction mixture was heated to reflux and held therefor 6 hours.
*Alkyl Pyridine R is a crude distillation bottoms with an eqv. weight of 170.

In a similar manner the following examples were prepared.

| Example | $N^{\oplus}CH_2CH_2SO_2CH_2CH_2N^{\oplus}$ $2X^{\ominus}$ <br> N N | X |
|---|---|---|
| 16 | (3-methylpyridinium) | Br |
| 17 | (acridine-like structure with CH, two C₆H₄, N) | Cl |
| 18 | (N-methylpiperidinium) | I |
| 19 | (N-methylmorpholinium) | Br |
| 20 | (triazabicyclic cage, N with three N) | Cl |
| 21 | (acridinium) | Cl |

USES

This invention relates to the inhibition of corrosion, particularly the corrosion of metals in contact with acid solutions.

The present invention is especially useful in the acidizing or treating of earth formations and wells traversed by a bore hole. It may also be used in metal cleaning and pickling baths which generally comprise aqueous solutions of inorganic acids such as sulfuric acid, hydrochloric acid, phosphoric acid and are useful in the cleaning and treatment of iron, zinc, ferrous alloys, and the like.

While the compounds of this invention are of themselves particularly good acid corrosion inhibitors, optionally they may be blended with acetylenic alcohols, dispersing and solubilizing agents such as ethoxylated alcohols and phenols.

USE IN BRINES

This phase of the invention relates to the prevention of corrosion in systems containing a corrosive aqueous medium, and most particularly in systems containing brines.

More particularly, this invention relates to the prevention of corrosion in the secondary recovery of petroleum by water flooding and in the disposal of waste water and brine from oil and gas wells. Still more particularly, this invention relates to a process of preventing corrosion in water flooding and in the disposal of waste water and brine from oil and gas wells which is characterized by injecting into an underground formation an aqueous solution containing minor amounts of compositions of this invention, in sufficient amounts to prevent the corrosion of metals employed in such operation. This invention also relates to corrosion inhibited brine solutions of these compounds.

When an oil well ceases to flow by the natural pressure in the formation and/or substantial quantities of oil can no longer be obtained by the usual pumping methods, various processes are sometimes used for the treatment of the oilbearing formation in order to increase the flow of the oil. These processes are usually described as secondary recovery processes. One such process which is used quite frequently is the water flooding process wherein water is pumped under pressure into what is called an "injection well" and oil, along with quantities of water, that have been displaced from the formation, are pumped out of an adjacent well usually referred to as a "producing well." The oil which is pumped from the producing well is then separated from the water that has been pumped from the producing well and the water is pumped to a storage reservoir from which it can again be pumped into the injection well. Supplementary water from other sources may also be used in conjunction with the produced water. When the storage reservoir is open to the atmosphere and the oil is subject to aeration this type of water flooding system is referred to herein as an "open water flooding system."

Because of the corrosive nature of oil field brines to economically produce oil by water flooding, it is necessary to prevent or reduce corrosion since corrosion increases the cost thereof by making it necessary to repair and replace such equipment at frequent intervals.

I have now discovered a method of preventing corrosion in systems containing a corrosive aqueous media, and most particularly in systems containing brines, which is characterized by employing the compositions of this invention.

I have also discovered an improved process of protecting from corrosion metallic equipment employed in secondary oil recovery by water flooding such as injection wells, transmission lines, filters, meters, storage tanks, and other metallic implements employed therein and particularly those containing iron, steel, and ferrous alloys, such process being characterized by employing in water flood operation the compositions of this invention.

This phase of the invention then is particularly concerned with preventing corrosion in a water flooding process characterized by the flooding medium containing an aqueous or an oil field brine solution of these compounds.

In many oil fields large volumes of water are produced and must be disposed of where water flooding operations are not in use or where water flooding operations cannot handle the amount of produced water. Most states have laws restricting pollution of streams and land with produced water, and oil producers must then find some method of disposing of the waste produced salt water. In many instances, therefore, the salt water is disposed of by injecting the water into permeable low pressure strata below the fresh water level. The formation into which the water is injected is not the oil producing formation and this type of disposal is defined as salt water disposal or waste water disposal. The problems of corrosion of equipment are analogous to those encountered in the secondary recovery operation by water flooding.

The compositions of this invention can also be used in such water disposal wells thus providing a simple and economical method of solving the corrosion problems encountered in disposing of unwanted water.

Water flood and waste disposal operations are too well known to require further elaboration. In essence, in the present process, the flooding operation is effected in the conventional manner except that the flooding medium contains a minor amount of the compound of this invention, sufficient to prevent corrosion, in concentrations of about 10 p.p.m. to 10,000 p.p.m., or more, for example, about 50 to 5,000 p.p.m., but preferably about 15 to 1,500 p.p.m. The upper limiting amount of the compounds is determined by economic considerations. Since the success of a water flooding operation manifestly depends upon its total cost being less than the value of the additional oil recovered from the oil reservoir, it is quite important to use as little as possible to these compounds consistent with optimum corrosion inhibition. Optimum performance is generally obtained employing about 1,000 p.p.m. Since these compounds are themselves inexpensive and are used in low concentrations, they enhance the success of a flood operation by lowering the cost thereof.

STATIC WEIGHT LOSS TEST

These tests are run on both synthetic and naturally occurring fluids. The test procedure involves the measurement of the corrosive action of fluids inhibited by the compositions herein described upon sandblasted AISI 1020 steel coupons measuring $\frac{3}{8} \times 3\frac{1}{4}$ inches under conditions approximating those found in an actual producing well, and the comparison thereof with results obtained by subjecting identical test coupons to the corrosive action of identical fluids containing no inhibitor.

Clean pint bottles were charged with 200 ml of 10% sodium chloride solution saturated with $H_2S$ and 200 ml. mineral spirits and a predetermined amount of inhibitor was then added. In all cases the inhibitor concentration was based on the total volume of the fluid. Weighed coupons were then added, the bottles tightly sealed and allowed to remain at room temperature for 3 days. The coupons were then removed, cleaned by immersion in inhibited 10% HCl, dried and weighed.

The changes in the weight of the coupons during the corrosion test were taken as a mesurement of the effectiveness of the inhibitor compositions. Protection percentge was calculated for each test coupon taken from the inhibited fluids in accordance with the following formula:

$$\frac{L_1 - L_2}{L_1} \times 100 = \% \text{ Protection}$$

in which $L_1$ is the loss in weight of the coupons taken from uninhibited fluids and $L_2$ is the loss in weight of coupons which were subjected to the inhibited fluids.

Table 1

| | Static Weight Loss Test | |
|---|---|---|
| Example | p.p.m. | % Protection |
| 2 | 40 | 98.5 |
| 3 | 40 | 98.7 |
| 7 | 40 | 99.2 |
| 13 | 40 | 96.5 |
| 15 | 40 | 99.5 |
| 19 | 40 | 96.8 |

USE IN AIR DRILLING

It has long been conventional practice in drilling deep bore holes to circulate a drilling mud down through the drill stem and up through the bore hole between the wall of the bore hole and the drill stem for the removal of chips or cuttings from the bore hole and to provide support for the wall of the bore hole. More recently, in the drilling of holes in which wall support provided by drilling mud is not employed, drilling has been carried out with the use of air for chip removal. Such drilling is not only normally faster than mud drilling, but is indispensable in areas where the supply of water is limited or when drilling through cavernous formations into which the drilling and mud flows and becomes lost.

The increasing popularity of air or gas drilling has come about not only because this method of drilling is frequently faster, as noted above, but for the additional reasons that the drill bits last longer, the provision and handling of water under wide ranges of temperature conditions is avoided, boring samples are easily observed when they are not mixed with mud, and there is no loss involved as in the case of mud drilling when drilling through cavernous formations. Furthermore, prompt removal of water entering the hole maintains a dry hole and the likelihood of wall collapse is thereby reduced.

In a typical air drilling operation there may be provided, for example, an up-flow of air in the bore hole having a velocity of the order of 3,000 feet per minute. This flow of air upwardly through the bore hole, which is produced by air pumped downwardly through the drill stem, provides adequate removal of cuttings. The air is delivered to the drill stem at pressures of 20 to 60 lbs. per square inch and for dewatering or for breaking obstructions, as will be hereinafter described, the pressures may be increased to 180 to 200 lbs. or more per square inch.

Air drilling operations are frequently hampered by the inflow of water into the bore hole when the drill bit is penetrating a water bearing stratum or when the bore hole has passed through a water bearing stratum that has not been cased. Normally, if drilling proceeds uninterruptedly both before and during penetration into a water bearing stratum, the flow of air is sufficient to blow the water out of the bore hole along with the cuttings and drilling dirt. There are, however, two major problems encountered in air drilling when water is entering the bore hole. The first problem occurs when there is a small inflow of water sufficient to cause a dampening of the cuttings which, under certain conditions, will then ball-up, clogging and sometimes jamming the drill bit. The second problem is encountered when there is a substantial amount of water remaining in the bottom of the bore hole during drilling causing a sloughing of the side wall of the bore hole. This latter condition may arise even though the water entering the bore hole is being blow out of the hole as fast as it enters. If there is a substantial inflow of water or if there is a substantial flow of water past a region of the bore hole susceptible to this condition, the water passing that region of the bore hole may cause a sloughing of the side wall.

The addition of foam forming materials to the air flow when air drilling is employed in conjunction with sufficient water to provide foaming gives rise to numerous advantages in drilling operation. The water may be introduced either through a water bearing stratum being penetrated by the drill bit or, alternatively, if the hole is dry, water may be introduced from the surface of the earth through the drill stem in conjunction with the delivery of compressed air and foam forming material through the drill stem to the drill bit. In either case the water may be said to be existing in the bore hole, and drilling operations are described in U.S. Pat. No. 3,130,798.

The amount of the compositions of the invention to be employed as a corrosion inhibitor can vary widely depending upon particular compounds, the particular system, the amounts of oxygen present, etc. I may employ concentrations of from about 0.5 to 5,000 p.p.m., such as from about 4 to 4,000 p.p.m., for example from about 20 to 2,000 p.p.m., but preferably from about 100 to 1,000 p.p.m. The optimum amount, to be determined in each instance, which will depend on function and economics, can be lesser or greater than the above amounts under proper conditions.

In addition, these compounds are not sensitive to oxygen content of the water and these are effective corrosion inhibitors in both open water flooding systems and closed water flooding systems.

While the flooding medium employed in accordance with the present invention contains water or oil field brine and the compounds, the medium may also contain other materials. For example, the flooding medium may also contain other agents such as surface active agents or detergents which aid in wetting throughout the system and also promote the desorption of residual oil from the formation, sequestering agents which prevent the deposition of calcium and/or magnesium compounds in the interstices of the formation, bactericides which prevent the formation from becoming plugged through bacterial growth, tracers, etc. Similarly, they may be employed in conjunction with any of the operating techniques commonly employed in water flooding and water disposal processes, for example five spot flooding, peripheral flooding, etc., and in conjunction with other secondary recovery methods.

Numerous tests were performed which demonstrate the effectiveness of the compositions of this invention as corrosion inhibitors for the protection of metals in contact with water. In these tests, AlSl 1010 steel coupons were weighed and placed in beakers containing about 1 liter of 3% sodium chloride at 70° F and various amounts of the corrosion inhibitors.

In addition air was bubbled through each solution for the duration of the test which lasted for 24 hours. The coupons were withdrawn and the corrosion products on the coupons were removed by using a soft brush. The coupons were rinsed with distilled water and reweighed. The loss in weight (in mg.) was then inserted into the equation:

(KW/DAT) = corrosion in mills/yr.

wherein
W = weight loss during tests in mg.;
D = specific gravity of the metal;
A = exposed surface area in sq. cm.%
T = time of exposure to solution in hrs.;
K = 3402

Table 2

| Corrosion rates on mild steel coupons in contact with water. | | |
|---|---|---|
| Corrosion Inhibitor Ex. | p.p.m. | Corrosion rates m.p.y. |
| 3 | 300 | 6.1 |
| 7 | 300 | 5.1 |
| 15 | 300 | 2.3 |
| Corrosion medium | — | 25.8 |

USE IN ACID SYSTEMS

The compounds of this invention can also be employed as corrosion inhibitors for acid systems, for example as illustrated by the pickling of ferrous metals, the treatment of calcareous earth formations, etc., as described in the following sections.

USE IN ACIDIZING EARTH FORMATIONS

The compositions of this invention can also be used as corrosion inhibitors in acidizing media employed in the treatment of deep wells to reverse the production of petroleum or gas therefrom and more particularly to an improved method of acidizing a calcareous or magnesium oil-bearing formation.

It is well known that production of petroleum or gas from a limestone, dolomite, or other calcareous-magnesium formation can be stimulated by introducing an acid into the producing well and forcing it into the oil or gas-bearing formation. The treating acid, commonly a mineral acid such as HCl, is capable of forming water soluble salts upon contact with the formation and is effective to increase the permeability thereof and augment the flow of petroleum to the producing well.

A minor amount of the compound is generally employed sufficient to impart corrosion protection to the system. In general one employs concentration of trace amounts such as from about 1.0 p.p.m. to 10,00 p.p.m., for example from 5 to 5,000 p.p.m., such as from 100 to 2,500 p.p.m., but preferably from 500 to 2,000 p.p.m. In practice, concentrations of 1,000 ± 2,000 p.p.m., are employed.

CORROSION TEST PROCEDURE

AlSl 1020 coupons with a total surface area of 6.15 sq. in. were pickled in 10% HCl solution for 10 minutes, neutralized in a 10% solution of $NaHCl_3$, dipped in acetone and dried in a desiccator. 150 ml. of 15% HCl was poured into each of the test bottles. The inhibitor was then added. The bottles were placed in a water bath that had been heated to the desired test temperature and were preheated for 20 minutes. After which time, the coupons were placed in the preheated inhibited acid solutions. The coupons were left in the acid solutions for the specified test time, then removed, neutralized, recleaned, rinsed, dipped in acetone, allowed to dry, and then reweighed.

The loss in weight in grams was multiplied times a calculated factor to convert the loss in weight to $lbs./ft^2/24$ hrs. The factor was calculated as follows:

$$\frac{\frac{144 \text{ in.}^2}{ft^2}}{\frac{454 \text{ g}}{lb} \times \text{surface area of coupon (in}^2) \times \frac{1 \text{ day}}{24 \text{ hrs}}}$$

Table 3
Corrosion Inhibitor in 15% HCl

| Inhibitor | p.p.m. | Test Temp. | Test Time | Corrosion Rate (lbs/ft$^2$/day) |
|---|---|---|---|---|
| Ex. 2 | 2000 | 150° F | 4 Hrs. | 0.039 |
| Ex. 3 | " | " | " | 0.029 |
| Ex. 7 | " | " | " | 0.041 |
| Ex. 13 | " | " | " | 0.075 |
| Ex. 14 | " | " | " | 0.030 |
| Ex. 15 | " | " | " | 0.031 |
| Ex. 19 | " | " | " | 0.045 |
| Ex. 21 | " | " | " | 0.025 |

USE AS A MICROBIOCIDE

I. IN WATER TREATMENT

This phase of the present invention relates to the treatment of water. More particularly, it is directed to providing improved means for controlling microbiological organisms including bacteria, fungi, algae, protozoa, and the like, present in water.

It is well known that ordinary water contains various bacteria, fungi, algae, protozoa, and other microbiological organisms which, if uncontrolled, multiply under certain conditions so as to present many serious problems. For example, in swimming pools the growth of these microbiological organisms is very undesirable from a sanitary standpoint as well as for general appearances and maintenance. In industrial water systems such as cooling towers, condenser boxes, spray condensers, water tanks, basins, gravel water filters, and the like, microbiological organisms may interfere greatly with proper functioning of equipment and result in poor heat transfer, clogging of systems and rotting of wooden equipment, a well as many other costly and deleterious effects.

In other industrial applications where water is used in processes, as for example, a a carrying medium, etc., microbiological organisms may also constitute a problem in maintenance and operation. Illustrative of such industrial applications are the pulp and paper manufacturing processes, oil well flooding operations and the like.

The products of this invention are suitable as biocides for industrial, agricultural and horticultural, military, hygienic and recreational water supplies. They provide an inexpensive, easily prepared group of products which can be used, in minimal amounts, in water supplies, in cooling towers, air-conditioning systems, on the farm and ranch, in the factory, in civilian and military hospitals and dispensaries, in camps, for swimming pools, baths and aquaria, waterworks, wells, reservoirs, by fire-fighting agencies, on maritime and naval vessels, in boilers, steam-generators and locomotives, in pulp and paper mills, for irrigation and drainage, for sewage and waste disposal, in the textile industry, in the chemical industries, in the tanning industry, et cetera, and which will render said water supplies bactericidal, fungicidal and algicidal. They further provide a simple process whereby water supplies. for whatever purposes intended, are rendered bacteriostatic, fungistatic and aligistatic, i.e., said water supplies treated by the process of this invention will resist and inhibit the further growth or proliferation of bacteria, fungi, algae and all forms of microbial life therein.

II. WATER FLOODING IN SECONDARY RECOVERY OF OIL

This phase of the present invention relates to secondary recovery of oil by water flooding operations and is more particularly concerned with an improved process for treating flood water and oil recovery therewith. More particularly this invention relates to a process of inhibiting bacterial growth in the recovery of oil from oil-bearing strata by means of water flooding taking place in the presence of sulfate-reducing bacteria.

Water flooding is widely used in the petroleum industry to effect secondary recovery of oil. By employing this process the yield of oil from a given field may be increased beyond then 20 — 30 percent of the oil in a producing formation that is usually recovered in the primary process. In flooding operations, water is forced under pressure through injection wells into or under oil-bearing formations to displace the oil therefrom to adjacent producing wells. The oil-water mixture is usually pumped with the producing wells into a receiving tank where the water, separated from the oil, is siphoned off, and the oil then transferred to storage tanks. It is desirable in carrying out this process to maintain a high rate of water injection with a minimum expenditure of energy. Any impediment to the free entry of water into oil bearing formations seriously reduces the efficiency of the recovery operation.

The term "flood water" as herein employed is any water injected into oil-bearing formations for the secondary recovery of oil. In conventional operations, the water employed various from relatively pure spring water to brine and is inclusive of water reclaimed from secondary recovery operations and processed for recycling. The problems arising from the water employed depend in part on the water used. However, particularly troublesome and common to all types of water are problems directly or indirectly concerned with the presence of microorganisms, such as bacteria, fungi and algae. Microorganisms may impede the free entry of water into oil-bearing formations by producing ions susceptible of forming precipitates, forming slime and/or existing in sufficiently high numbers to constitute an appreciable mass, thereby plugging the pores of the oil-bearing formation. Pore plugging increases the pressure necessary to drive a given volume of water into an oil-bearing formation and oftentimes causes the flooding water to by-pass the formation to be flooded. In addition, microorganisms may bring about corrosion by acting on the metal structures of the wells involved, producing corrosive substances such as hydrogen sulfide, or producing conditions favorable to destructive corrosion such as decreasing the pH or producing oxygen. The products formed as the result of corrosive action may also be pore-plugging precipitates. Usually, the difficulties encountered are a combination of effects resulting from the activity of different microorganisms.

Organisms of the Desulfovibrio genus, more commonly known as sulfate reducing bacteria, are known particularly to preclude efficient operation of oil recovery by conventional water flooding techniques by producing $H_2S$ which reacts with iron or iron salts to precipitate black ferrous sulfide. These organisms are often resistant to the effects of many known antimicrobial compounds.

I have discovered that the compositions of this invention are effective bactericides for sulfate reducing bacteria.

III. HYDROCARBON TREATMENT

This phase of the present invention relates to the use of these compounds as biocides in hydrocarbon systems.

In addition to bring used as biocides in aqueous systems, the compounds of this invention can also be employed as biocides in hydrocarbon systems, particularly when petroleum products are stored. It is believed that bacteria and other organisms, which are introduced into hydrocarbon systems by water, feed readily on hydrocarbons resulting in a loss in product, that microorganisms cause the formation of gums, $H_2S$, peroxides, acids and slimes at the interface between water and oil; that bacterial action is often more pronounced with rolling motion than under static conditions, etc. Loss of product, corrosion of the storage tank, clogging of filters and metering instruments, and fuel deterioration are among the harmful effects of bacteria growth in fuels. The activity of microorganism growth is often increased by the presence of rust. Not only do these microorganisms often encourage rust but rust encourages microorganism growth. Since microorganism growth appears to be considerably higher with kerosene than with gasoline, plugged filters experienced with jet fuels which contain large amounts of kerosene is a serious problem.

The compositions of this invention can be employed in hydrocarbon systems.

MICROBIOCIDAL TESTING

A 1% by weight solution of the test compound in water was prepared. The solution was aseptically added to a sterile broth that would support the growth of the test organism, Desulfovibrio desulfuricans, to provide a concentration of 10, 25, 50 and 75 parts by weight of test compound per million parts by weight of broth. A general growth medium, such as prescribed by the American Petroleum Institute was used. The broth containing the test compound then was dispersed in 5 cc. amounts into sterile disposable tubes and the tubes were inoculated with the growing test organism and incubated at 90°–100° F for 72 hrs. The absence or presence of growth of the microorganism was determined visually by an experienced observer.

Table 4

| Results of microbiocide test | Concentration of test compound |
|---|---|
| Ex. 2 | 25 |
| Ex. 3 | 25 |
| Ex. 4 | 50 |
| Ex. 7 | 25 |
| Ex. 10 | 25 |
| Ex. 12 | 75 |
| Ex. 16 | 50 |
| Ex. 20 | 50 |

In all of the above tests no growth of the test organism occurred, thus indicating that the compound is a biostat or a biocide.

As is quite evident, other Bis-Quaternaries prepared by reacting amines and divinyl sulfur compounds will be constantly developed which could be useful in this invention. It is, therefore, not only impossible to attempt a comprehensive catalogue of such compounds, but to atempt to describe the invention in its broader aspects in terms of other specific compounds used would be tool voluminous and unnecessary since one skilled in the art could by following the description of the invention herein select useful cyclic amines and divinyl sulfur compounds. To precisely define each specific useful tertiary amine and divinyl sulfur compound employed in preparing Bis-Quaternaries in light of the present disclosure would merely call for chemical knowledge within the skill of the art in a manner analogous to a mechanical engineer who prescribes in the construction of a machine the proper materials and the proper dimensions thereof. From the description in this specification and with the knowledge of a chemist, one will know or deduce with confidence the applicability of specific compounds suitable for this invention by applying them in the invention set forth herein. In analogy ton the case of a machine, wherein the use of certain materials of construction or dimensions of parts would lead to no practical useful result, various materials will be rejected as inapplicable where others would be operative. I can obviously assume that no one will wish to employ a useless compound nor will be misled because it is possible to misapply the teachings of the present disclosure to do so.

I claim:

1. A process of inhibiting corrosion which comprises treating a corrosive aqueous medium with Bis-quaternaries of the following formula:

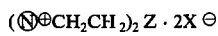

where  is a quaternary amino group, Z is the sulfur-containing group S, SO, or $SO_2$ and X is an anion.

2. The process of claim 1 where Z is $SO_2$.

3. The process of claim 1 where the formula is

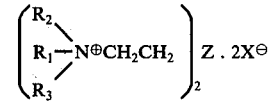

where $R_1$, $R_2$ and $R_3$ are alkyl or oxygen-containing alkyl groups.

4. The process of claim 1 where the formula is $$(\text{\textcircled{N}} \oplus CH_2CH_2)_2 Z \cdot 2X^\ominus$$

where ⓝ is a cyclic tertiary amine moiety.

5. The process of claim 3 where Z is $SO_2$.

6. The process of claim 4 where Z is $SO_2$.

7. The process of claim 1 where the ⓝ⊕ is an aliphatic tertiary amino group or a heterocyclic tertiary amino group.

8. The process of claim 3 where $R_1$, $R_2$ and $R_3$ are alkylene oxyalkylene or hydroxy alkyl groups.

9. The process of claim 4 where ⓝ is a pyridine radical.

10. The process of claim 3 where $R_1$ and $R_2$ are methyl and $R_3$ is dodecyl.

* * * * *

UNITED STATES PATENT AND TRADEMARK OFFICE
CERTIFICATE OF CORRECTION

PATENT NO. : 4,057,390
DATED : November 8, 1977
INVENTOR(S) : Patrick M. Quinlan It is certified that error appears in the above-identified patent and that said Letters Patent are hereby corrected as shown below:

Column 2, the third formula should read

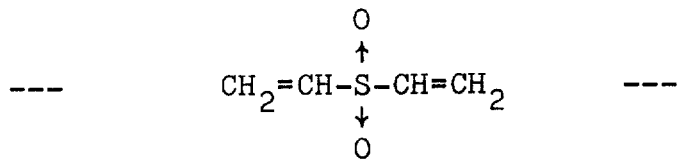

---      ---

Column 3, line 13, "0.01" should read

---    0.1    ---

Column 10, line 3, after "CORROSION TEST PROCEDURE", "$NaHCl_3$" should read

---    $NaHCO_3$    ---

Signed and Sealed this

Twenty-fifth Day of April 1978

[SEAL]

Attest:

RUTH C. MASON
Attesting Officer

LUTRELLE F. PARKER
Acting Commissioner of Patents and Trademarks